(12) United States Patent
Raday et al.

(10) Patent No.: US 8,870,832 B2
(45) Date of Patent: Oct. 28, 2014

(54) VIAL ADAPTOR AND MANUFACTURING METHOD THEREFOR

(75) Inventors: Lior Raday, Ashkelon (IL); Lior Mareli, Rehovot (IL); Ehud Carmel, Ganey Tikva (IL); David Daily, Herzliya (IL); Guy Keenan, Tel Aviv (IL)

(73) Assignee: Elcam Medical A.C.A.L Ltd, Kibbutz Baram (IL)

( * ) Notice: Subject to any disclaimer, the term of this patent is extended or adjusted under 35 U.S.C. 154(b) by 721 days.

(21) Appl. No.: 12/741,628

(22) PCT Filed: Nov. 10, 2008

(86) PCT No.: PCT/IB2008/054701
§ 371 (c)(1),
(2), (4) Date: Jul. 15, 2010

(87) PCT Pub. No.: WO2009/060419
PCT Pub. Date: May 14, 2009

(65) Prior Publication Data
US 2010/0286661 A1    Nov. 11, 2010

Related U.S. Application Data

(60) Provisional application No. 61/002,675, filed on Nov. 8, 2007.

(51) Int. Cl.
| | | |
|---|---|---|
| A61M 5/00 | (2006.01) | |
| A61M 5/24 | (2006.01) | |
| A61M 5/28 | (2006.01) | |
| A61M 5/20 | (2006.01) | |
| A61J 1/20 | (2006.01) | |
| A61M 5/178 | (2006.01) | |

(52) U.S. Cl.
CPC ........ *A61J 1/2096* (2013.01); *A61J 2001/2065* (2013.01); *A61J 2001/2055* (2013.01); *A61M 5/2033* (2013.01); *A61J 2001/201* (2013.01); *A61M 5/1782* (2013.01)
USPC .......................................... 604/234; 604/205

(58) Field of Classification Search
USPC .............. 604/87, 88, 200–206, 232, 234, 520
See application file for complete search history.

(56) References Cited

U.S. PATENT DOCUMENTS

| | | | |
|---|---|---|---|
| 4,211,588 A | 7/1980 | Raines | |
| 4,588,403 A | 5/1986 | Weiss | |

(Continued)

FOREIGN PATENT DOCUMENTS

| | | |
|---|---|---|
| EP | 0 435 860 | 7/1991 |
| EP | 0435860 | 7/1991 |

(Continued)

OTHER PUBLICATIONS

An Office Action dated Jul. 7, 2011, which issued during the prosecution of Canadian Patent Application No. 2,539,315.

*Primary Examiner* — Nathan R Price
(74) *Attorney, Agent, or Firm* — Stein IP LLC

(57) ABSTRACT

A vial adaptor for releasably holding a vial (1010) and releasable connection to an injector (1008) comprising: a dual-sleeved member (11) comprising a forward facing sleeve (12) and a rearward facing sleeve (16) adapted to operably engage a front end of a forward housing (1040) of said injector (1008), and comprising a vial stopper piercing member (46); and a vial engaging element (60) adapted to slidingly translate within said forward facing sleeve (12) and releasibly hold said vial (1010) in a position whereby said vial stopper piercing member (46) pierces a stopper of said vial (1010), said vial engaging element (60) adapted to allow forward movement of a plunger of said injector (1008) when said vial (1010) is in said position. In other aspects, a vial-stopper piercing spike and a method of manufacturing same is described.

14 Claims, 11 Drawing Sheets

(56) References Cited

U.S. PATENT DOCUMENTS

| | | | |
|---|---|---|---|
| 4,662,878 A | 5/1987 | Lindmayer | |
| 4,759,756 A | 7/1988 | Forman | |
| 4,850,978 A | 7/1989 | Dudar | |
| 4,883,483 A | 11/1989 | Lindmayer | |
| 5,171,214 A | 12/1992 | Kolber | |
| 5,232,029 A | 8/1993 | Knox | |
| 5,356,380 A | 10/1994 | Hoekwater | |
| 5,385,547 A | 1/1995 | Wong | |
| 5,397,303 A | 3/1995 | Sancoff | |
| 5,423,753 A | 6/1995 | Fowles | |
| 5,445,631 A | 8/1995 | Uchida | |
| 5,466,220 A | 11/1995 | Brenneman | |
| 5,478,316 A | 12/1995 | Bitdinger et al. | |
| 5,527,306 A | 6/1996 | Haining | |
| 5,766,147 A | 6/1998 | Sancoff | |
| 5,776,125 A | 7/1998 | Dudar et al. | |
| 5,919,182 A | 7/1999 | Avallone | |
| 6,139,534 A | 10/2000 | Niedospial, Jr. | |
| 6,270,479 B1 | 8/2001 | Bergens et al. | |
| 6,358,236 B1 | 3/2002 | DeFoggi | |
| 6,364,865 B1 * | 4/2002 | Lavi et al. | 604/411 |
| 6,378,576 B2 | 4/2002 | Thibault | |
| 6,378,714 B1 | 4/2002 | Jansen | |
| 6,503,240 B1 | 1/2003 | Niedospial, Jr. | |
| 6,544,246 B1 | 4/2003 | Niedospial, Jr. | |
| 6,601,721 B2 | 8/2003 | Jansen | |
| 6,607,508 B2 | 8/2003 | Knauer | |
| 6,875,613 B2 | 4/2005 | Shartle | |
| 6,901,975 B2 | 6/2005 | Aramata | |
| 6,945,417 B2 | 9/2005 | Jansen | |
| 6,948,522 B2 | 9/2005 | Newbrough | |
| 6,957,745 B2 | 10/2005 | Thiebault | |
| 7,354,427 B2 | 4/2008 | Fangrow | |
| 7,569,043 B2 | 8/2009 | Fangrow | |
| 7,615,041 B2 | 11/2009 | Sullivan | |
| 2004/0073189 A1 | 4/2004 | Wyatt | |
| 2004/0199139 A1 | 10/2004 | Fowles et al. | |
| 2005/0124964 A1 | 6/2005 | Niedospial, Jr. et al. | |
| 2006/0025747 A1 | 2/2006 | Sullivan et al. | |
| 2006/0086750 A1 * | 4/2006 | Geyer et al. | 222/81 |
| 2007/0016161 A1 | 1/2007 | Costa | |
| 2007/0088313 A1 | 4/2007 | Zinger et al. | |
| 2007/0088315 A1 | 4/2007 | Haindl | |
| 2007/0106244 A1 | 5/2007 | Mosler | |
| 2007/0156112 A1 | 7/2007 | Walsh | |
| 2008/0300536 A1 | 12/2008 | Wang | |
| 2008/0300570 A1 | 12/2008 | Fowles | |
| 2009/0015948 A1 | 1/2009 | Wada et al. | |
| 2009/0018230 A1 | 1/2009 | Chisholm et al. | |
| 2009/0159485 A1 | 6/2009 | Jakob et al. | |
| 2009/0182300 A1 | 7/2009 | Radmer | |
| 2009/0216213 A1 | 8/2009 | Muir | |

FOREIGN PATENT DOCUMENTS

| | | |
|---|---|---|
| EP | 0662851 | 7/1995 |
| EP | 0 662 851 | 9/1998 |
| EP | 2 133 059 A2 | 4/2005 |
| EP | 2079432 | 7/2009 |
| EP | 2 079 432 | 11/2010 |
| WO | WO 95/01197 | 1/1995 |
| WO | WO 02/47746 A1 | 6/2002 |
| WO | WO 03/011378 A1 | 2/2003 |
| WO | 2008046206 | 4/2008 |
| WO | WO 2008/046206 | 4/2008 |
| WO | WO/2008/047372 | 4/2008 |
| WO | WO 2008/047372 | 4/2008 |
| WO | WO 2008/048631 | 4/2008 |
| WO | WO 2008/093063 A2 | 8/2008 |

* cited by examiner

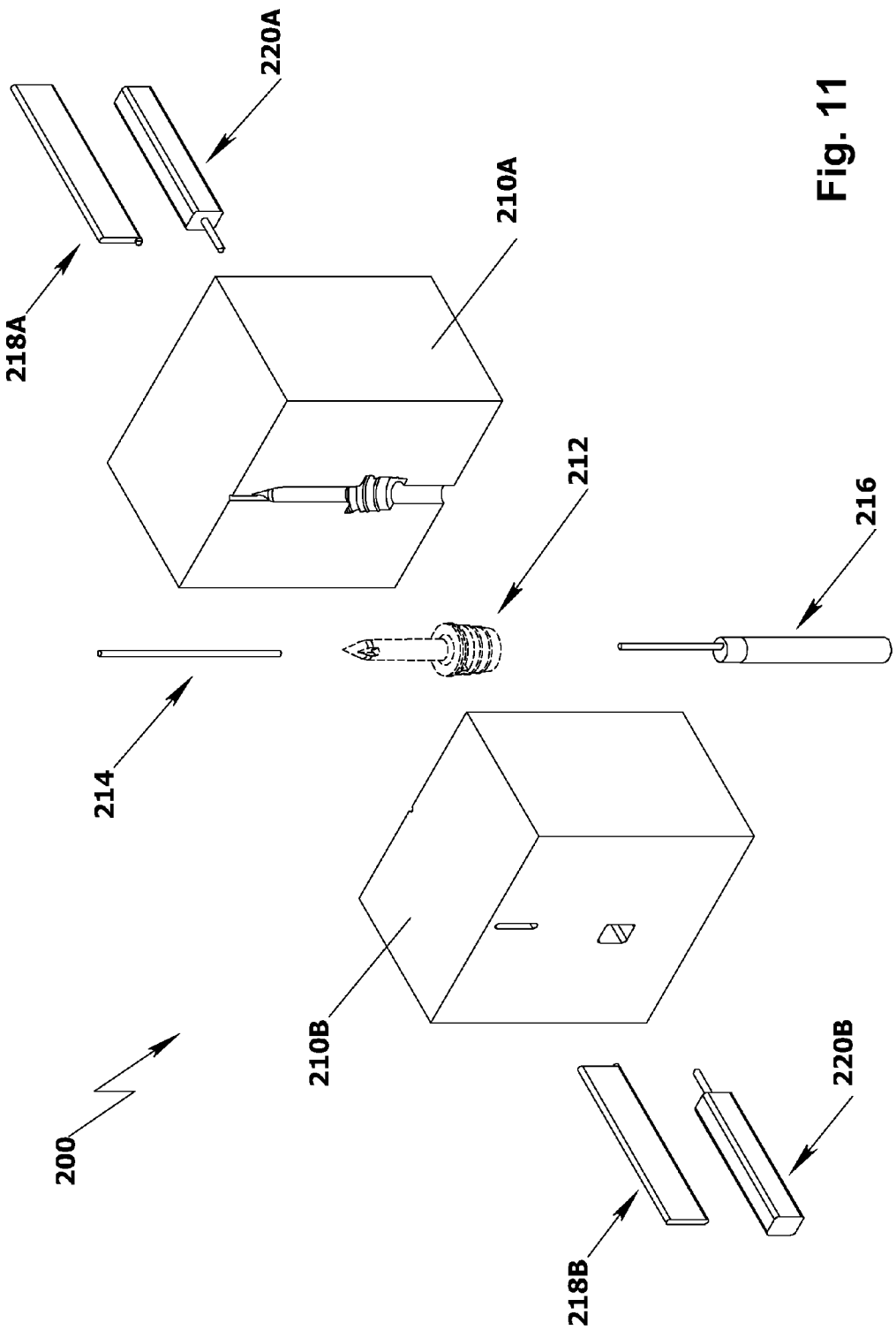

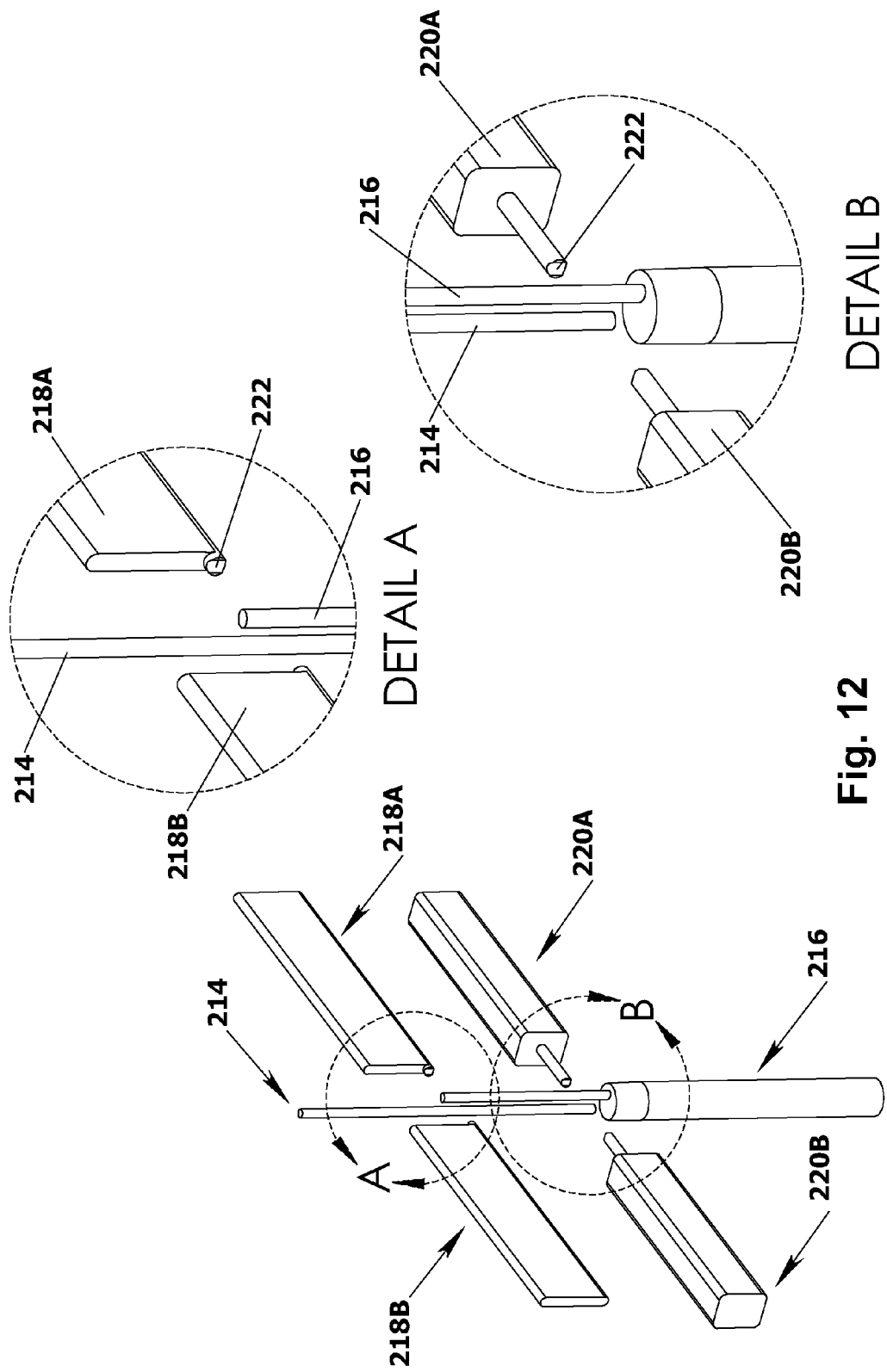

VIAL ADAPTOR AND MANUFACTURING METHOD THEREFOR

FIELD OF THE INVENTION

The present invention relates to an appliance for administering a medication, in particular a vial adaptor and a vial stopper-piercing member therefor and method of manufacturing the member.

BACKGROUND OF THE INVENTION

It is conventional to store drugs, vaccines, medicaments, solutions and the like (hereinafter, "medication(s)") in a sealed vial or other similar container for later use. Such medications may be stored in a dry or powdered form and reconstituted in liquid form for later use, by adding a solvent, for example; alternatively, the medication may be stored in a vial in a liquid form.

A conventional vial for storing medication has an open end, a radial rim surrounding the open end, a planar rim portion that overlies the vial rim, and a reduced diameter neck portion adjacent the rim. Commonly, such vials are closed by an elastomeric stopper, or other pierceable closure, which is pierced by a syringe.

Vial adaptors, which are disposed intermediate a vial and an injection device (hereinafter used interchangeably with the term "injector" or the like) are commonly used to aid in the withdrawal of medication from a vial. Such adaptors help to hold the vial; align the syringe with the vial's stopper; and avoid accidental pricking of a user's finger.

WO 2008/047372 discloses an example of an injection device for the withdrawal of medication from a vial and injection of the medication, the device including a vial adaptor and an injector.

Rigid (non-collapsible) vials require the influx of air when medication is withdrawn, to prevent the formation of a vacuum therein. For such purpose, among other purposes, vial adaptors have been developed; some of which include a bi-functional (e.g. dual-passage or dual-conduit) stopper-piercing member that pierces the vial's stopper and is designed to allow air to flow into the vial via one conduit while medication is being withdrawn via another conduit. Some vial adaptors have a filter at the air entrance of the air conduit to prevent entry of particulate matter or bacteria into the vials during the medicament withdrawal process and air influx (e.g. as disclosed in U.S. Pat. No. 5,766,147).

U.S. Pat. No. 5,766,147 also describes a bi-functional stopper-piercing member, referred to therein as a needle, depicted as grooves in the outer surface of the needle. A possible issue with such grooves is that the typically elastomeric, i.e. resilient, stopper may block or partially block the grooves. On the other hand, internal passages/conduits can be difficult to manufacture due to the small size and possibility of buckling of the mold pins creating the conduits as a result of temperature change, and/or manufacturing design, during the manufacturing process.

SUMMARY OF THE INVENTION

According to one aspect, the invention relates to an improved adaptor to aid in the activity of transferring fluid from a first container, such as a conventional medical vial having a pierceable closure or stopper, and a second container, such as an injection device (hereinafter also referred to as an "injector") and which simultaneously allows air flow, introducing filtered atmospheric air into the vial by means of single bi-functional (dual-conduit) stopper-piercing member (hereinafter also referred to as a "spike").

The adaptor, hereinafter also referred to as a "vial adapter" comprises two parts, an exterior part, which forms a dual sleeved housing for engaging with the injector; and an interior part (hereinafter also referred to as a "crown") that is movable within one sleeve of the exterior part and adapted for engaging with the vial. The crown is inwardly into a sleeve of the exterior part (housing) upon inserting the vial therein.

When the vial is inserted into the crown, a plunger locking mechanism of the injector is deactivated to allow withdrawal of medication from the vial and ejection of fluid back into the vial (or into a different vial if seated properly in the adaptor). Removal of the vial from the vial adapter will move the interior part in the vial removal direction locking the plunger locking mechanism to prevent ejection of fluid from the injector.

The vial adapter provides a convenient releasable attachment mechanism intermediate the vial and injector, and additionally provides easy manipulation and use as it is activated automatically upon vial insertion and prevents the possibility of human error.

It is a particular feature of the vial adaptor of the present invention that it is useable in combination with a conventional drug vial and an appropriate injector, to prevent accidental ejection of medication at inappropriate circumstances, however allows a liquid to be withdrawn from a first vial and ejected into the same or a different vial when the vial is seated (positioned) appropriately in the adaptor.

This feature is particularly suited to the preparation of a medication prepared by withdrawing a solvent from a first vial seated in the adaptor, removing that vial from the adaptor and placing a second vial containing a solid (e.g. powder), then injecting the solvent into the second vial; which can then be withdrawn into the injector for administering the medication.

An example of such a conventional vial and appropriate injector is described in WO 2008/047372, which is incorporated herein in its entirety. The vial adaptor is typically made of a plastic material, although not limited to any particular material.

Accordingly, the invention provides a vial adaptor for releasably holding a vial and having a releasable connection to an injector comprising: a dual-sleeved member comprising a forward facing sleeve and a rearward facing sleeve adapted to operably engage a front end of a forward housing of said injector, and comprising a vial stopper piercing member; and a vial engaging element adapted to slidingly translate within said forward facing sleeve and releasably hold said vial in a position whereby said vial stopper piercing member pierces a stopper of said vial establishing fluid communication between said vial and said injector and air communication between said vial and atmosphere, said vial engaging element adapted to allow forward movement of a plunger of said injector when said vial is in said position.

According to another aspect, the present invention relates to a bi-functional stopper-piercing member (hereinafter also referred to as a "spike") that provides a conduit for withdrawing fluid from a vial while allowing ambient air to enter to neutralize pressure in the vial via another conduit. The conduits are internal to the spike and thus cannot be blocked, or partially blocked, by an external member, such as the vial's stopper. The conduits are preferably spaced apart to the extent possible, to reduce the possibility of air, which tends to form bubbles when entering the vial, from entering the fluid withdrawal conduit. For this purpose, the ends of the conduits that pass into the vial are preferably located at different heights along the spike and face in opposite directions. Preferably, the outlet of the air conduit is adjacent the piercing end (tip) of the spike while the end of the fluid withdrawal conduit is set back from the spike's tip. At the non-piercing end of the spike there is preferably a base that aids in connecting the spike to the remainder of the vial adaptor. Typically, the conduits are parallel to each other and the longitudinal axis of the spike.

Accordingly, the present invention provides a spike adapted to pierce a vial-stopper, the spike comprising: an elongated needle with a piercing end and an opposite end; first and second spaced apart interior conduits generally parallel to the longitudinal axis of the needle, said first conduit extending from a point adjacent said piercing end to a point adjacent to or at the end of said opposite end of the needle and to an exterior surface of the spike, said second conduit extending from a point set back from said piercing end to a point adjacent to or at the end of said opposite end of the needle and to an exterior surface of the spike.

According to yet another aspect, the present invention relates to a method of producing a dual-conduit stopper-piercing member, which allows longitudinal thermal expansion and lateral stability to the mold pins that define the conduit during the molding process.

Accordingly, the present invention provides a method of producing a plastic spike with a dual interior conduits comprising: engaging a pair of molds to each other to form a mold assembly; introducing longitudinal pins between said molds; introducing lateral pins until their semi-circumferential recesses interface with said longitudinal pins; and injecting a molten polymer into said mold assembly.

BRIEF DESCRIPTION OF THE DRAWINGS

The invention may be understood upon reading of the following detailed description of non-limiting exemplary embodiments thereof, with reference to the following drawings, in which:

FIGS. 10 and 11 respectively show isometric and exploded views of an assembly of the molding parts used in an embodiment of a method of manufacturing a spike of the vial adaptor according to the present invention; and FIG. 12 is a more detailed view of particular components of FIGS. 10 and 11.

DETAILED DESCRIPTION OF PREFERRED EMBODIMENTS

The following detailed description of the invention refers to the accompanying drawings. Dimensions of components and features shown in the figures are chosen for convenience or clarity of presentation and are not necessarily shown to scale. Wherever possible, the same reference numbers will be used throughout the drawings and the following description to refer to the same and like parts.

Figure 1:
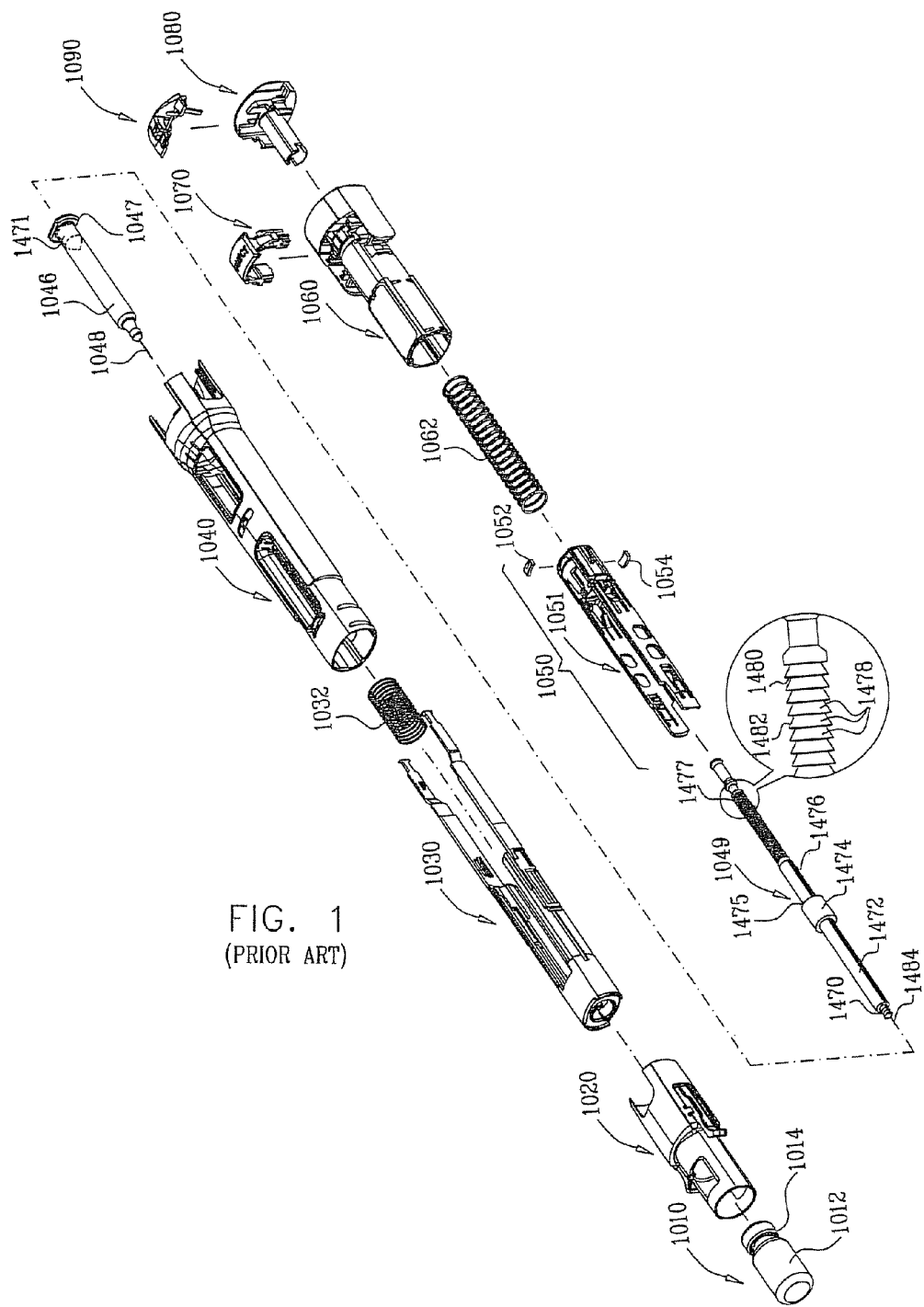
FIGS. 1 and 2 are an exploded view of a prior art injection device and an isometric view of an exemplary plunger locking element which forms part of the prior art automatic injection device of FIG. 1, respectively.
Figure 2:
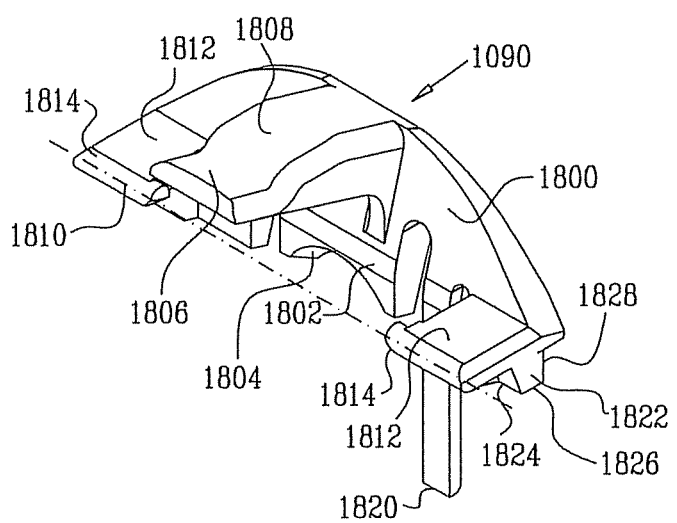

FIGS. 1 and 2 illustrate elements of a prior art injection device composed of an injector 1008; a typical container (herein after "drug vial" or "vial"; and designated as 1010); and a vial adaptor 1020 for connecting between the injector and vial. For understanding the vial adaptor of the present invention, designated with reference numeral 10, vial 1010 and injector 1008 will first be briefly described. It should be understood that the below described vial and injector are merely examples of a vial and an injector with which the present vial adaptor can be used.

Vial:

In FIG. 1 it is seen that vial 1010 includes a body portion 1012 and a neck and rim portion (partially seen), disposed below a crimped member 1014 for fastening an elastomeric seal (not shown) to the vial.

Injector:

FIG. 1 illustrates injector 1008, which typically has a needle guard 1030 that is positioned by a compression spring 1032 within a forward end of a forward housing 1040 to engage, at a front end thereof, vial adaptor 10. At each rearward most portion of free ends of arms 1319 of needle guard 1030 are upwardly and downwardly facing protrusions 1344 adapted to enable the release of the plunger 1049 from its locked orientation; detailed below. Needle guard 1030 is typically "right-to-left" symmetrical such that if the needle guard is turned over, upwardly and downwardly facing protrusions 1344 merely exchange directions with no effect on function; the oppositely facing protrusions merely easing assembly of injector 1008. At each side of forward housing 1040 (only one side seen), near its forward end, is a vial adaptor engaging recess 1041.

A syringe 1046, including a rear flange 1047 and having a hypodermic needle 1048 integrally formed therewith, is engaged by a plunger 1049. Syringe 1046 and plunger 1049 are typically located within forward housing 1040. Syringe 1046 may be a conventional syringe, such as a commercially available syringe sold under the catalog designation BD-Hypak™ or may be any other suitable syringe or cartridge.

Plunger 1049 selectably engages a selectable driving assembly 1050, which includes a selectable driving element 1051 and a pair of elastomeric motion damping elements 1052 and 1054. Selectable driving assembly 1050 is typically at least partially seated within a rear housing 1060, forward of a main compression spring 1062, which is also seated within rear housing 1060. Main compression spring 1062 provides selectable forward displacement to the selectable driving assembly 1050. Selectable operation of plunger 1049 by selectable driving assembly 1050 causes the plunger 1049 to inject liquid contents of syringe 1046 through hypodermic needle 1048.

Figure 3:
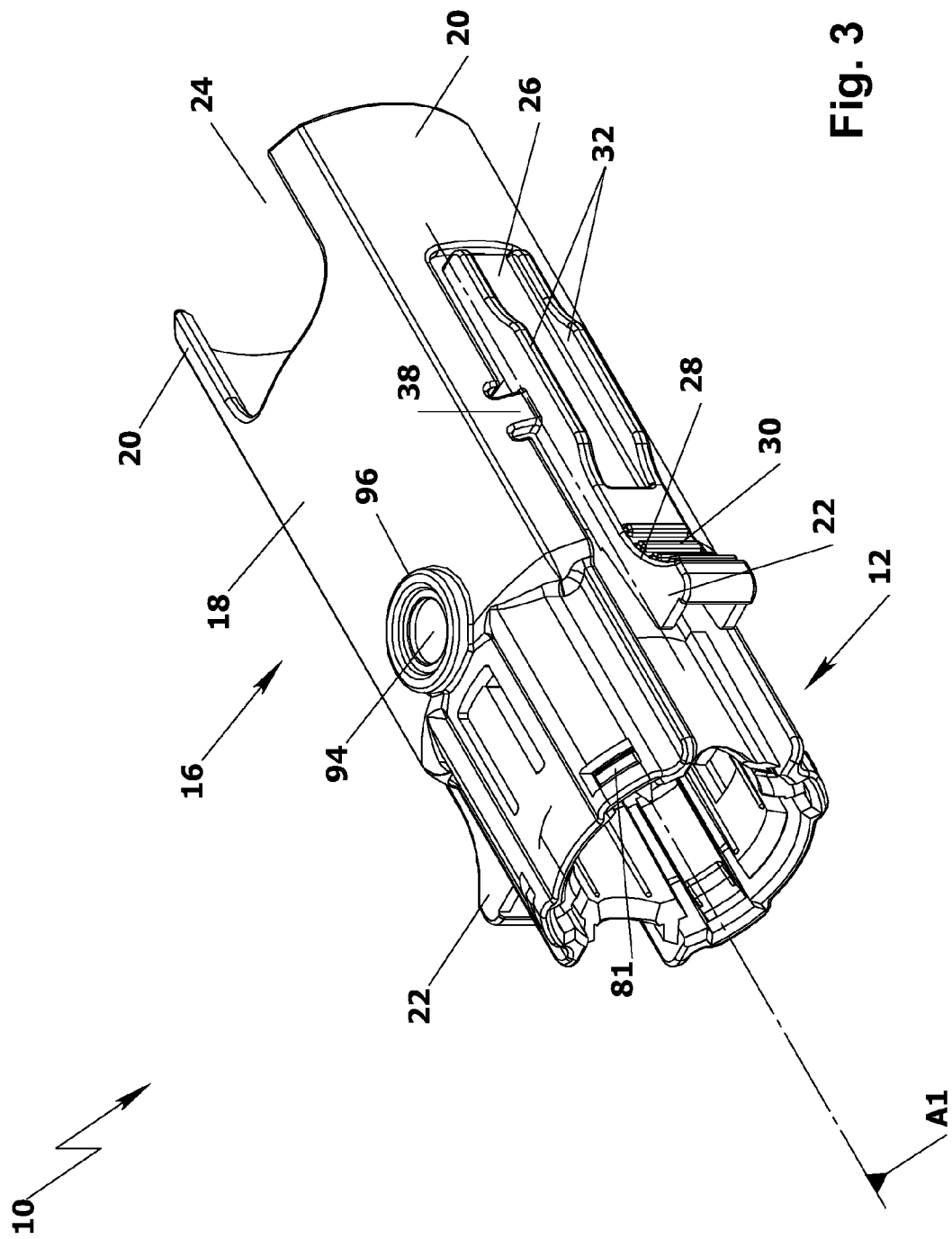
FIG. 3 is an isometric view of an embodiment of a vial adaptor in accordance with the present invention.

Plunger 1049 further includes a threaded protrusion 1470, which threadably engages a corresponding threaded socket (not shown) formed in a rear surface of a resilient piston 1471 which sealingly engages the interior of syringe 1046. Rearward of threaded protrusion 1470 is a generally circular cylindrical portion 1472 having a first cross sectional radius, followed by a relatively short circular cylindrical portion 1474 having a second cross sectional radius greater than the first radius and defining a rearward facing shoulder 1475. Rearward of portion 1474 is a third generally circular cylindrical portion 1476 having a third cross sectional radius, typically equal to the first radius. Rearward of portion 1476 is formed a toothed portion 1477, each tooth 1478 thereof having a generally transverse forwardly facing portion 1480 and a slanted rearwardly facing portion 1482. The particular shape of the teeth of toothed portion 1477 enables rearward movement of the plunger 1049 at any time, and requires a specific configuration of ejector 1008 in order to enable forward movement of the plunger 1049. Plunger 1049 is typically symmetrical about a longitudinal axis 1484, which, when the injector is assembled, is coaxial with a longitudinal axis A1 of vial adaptor 10 (FIG. 3).

Rear housing 1060 has associated therewith an actuation button 1070, operative to selectably actuate operation of selectable driving assembly 1050. Within rear housing 1060 are seated a rear end element 1080, operative to seal the rear end of the rear housing, and a plunger locking element 1090, cooperative with rear end element 1080 and operative to lock the plunger 1049 when contents of the syringe 1046 should not be injected through needle 1048.

FIG. 2 depicts details of the exemplary plunger locking element 1090 of FIG. 1. Plunger locking element 1090 includes an upright back portion 1800 having at a central bottom region thereof a plunger engaging protrusion 1802 having a curved bottom facing edge surface 1804 which is engageable with teeth 1478 of a toothed portion 1477 of the plunger 1049 (FIG. 1) to prevent the plunger 1049 from moving forward.

An actuation button engagement surface 1806 is provided on a forwardly extending protrusion 1808 of the top portion of plunger locking element 1090. Actuation button engagement surface 1806 is engaged by the underside of actuation button 1070 (FIG. 1) and is rotated thereby about an axis 1810 releasing the locking of the plunger 1049 during actuation of the injection device.

A pair of forwardly facing protrusions 1812, each having a curved forward end 1814, define axis 1810 about which plunger locking element 1090 rotates during actuation of the device. These protrusions are adapted to be seated in corresponding hemispherical recesses in the rear end element 1080 (not seen).

A resilient leg 1820 extends downwardly from back portion 1800, generally underneath one of forwardly facing protrusions 1812 and constantly urges plunger locking element 1090 to rotate about axis 1810 to a position in which plunger 1049 (FIG. 1) is locked (i.e. the plunger cannot move forward). When plunger locking element 1090 is rotated about axis 1810, resilient leg 1820 abuts against a forward facing protrusion of the rear end element 1080 (FIG. 1) and the plunger 1049 is released. A pair of downward facing protrusions 1822 (only one seen), each having a slanted forwardly facing surface 1824, a generally planar bottom surface 1826, and a generally planar rearwardly facing surface 1828, is formed on either of forwardly facing protrusions 1812 of the plunger locking element 1090.

During operation of the injector, such as during the injection stage, upwardly facing protrusions 1344 of arms 1319 of needle guard 1030 (FIG. 1) align with bottom surface 1826 of protrusions 1822, after rotation of the plunger locking element 1090 about axis 1810, thereby releasing the plunger 1049 (FIG. 1).

Vial Adaptor:

A preferred embodiment of vial adaptor 10 is now described with reference to FIGS. 3-9C. Vial adaptor 10 includes a dual-sleeved member 11 designed to operably and reversibly engage injector 1008, in particular the front end of needle guard 1030 thereof; and a vial engaging element or crown 60 that fits within one end of the dual facing body and is adapted to reversibly engage vial 1010. It is seen that vial adaptor 10 is typically side-to-side symmetric about its longitudinal axis A1 (FIG. 3).

Figure 4:
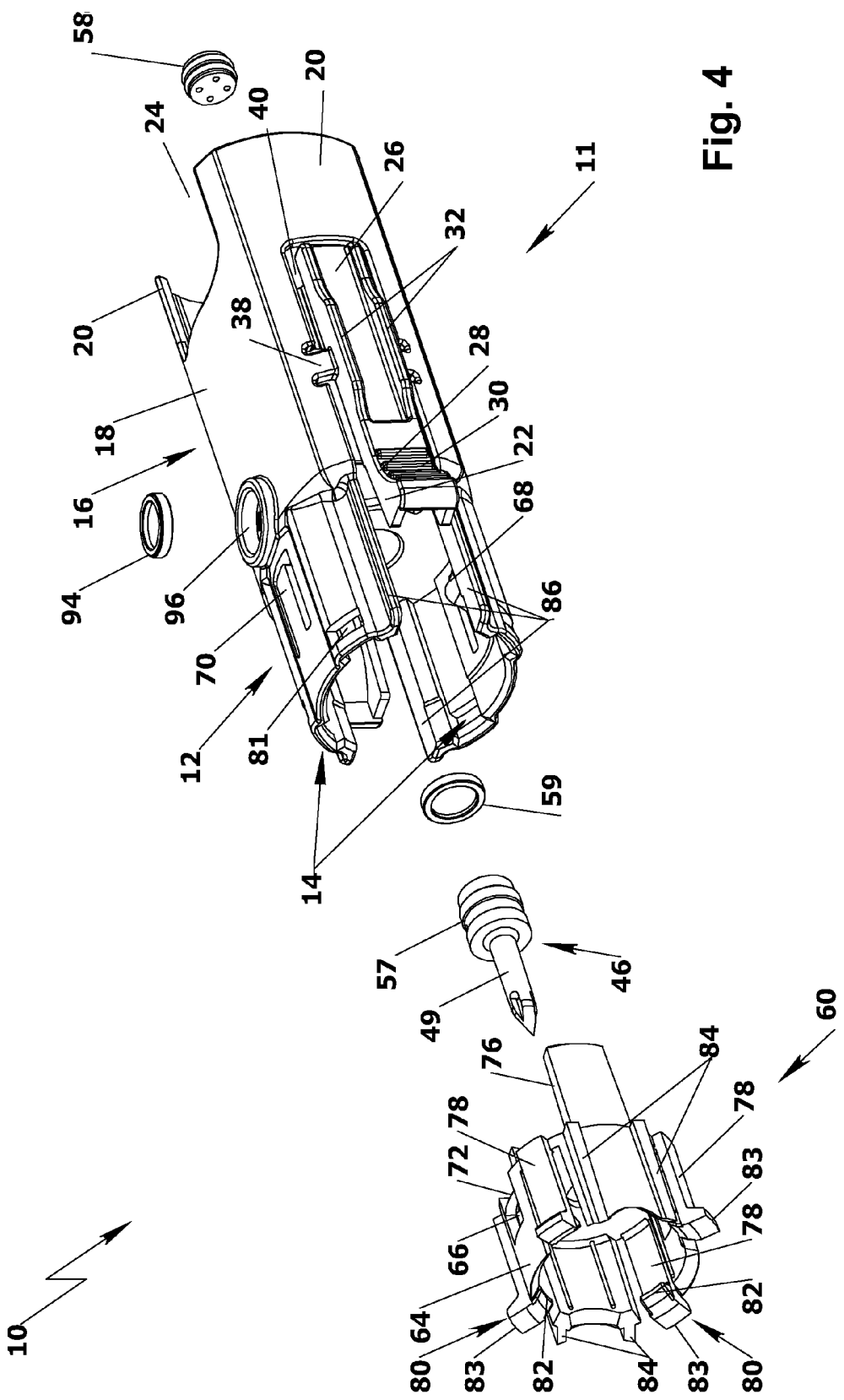
FIG. 4 is an exploded view of FIG. 3.
Figure 5:
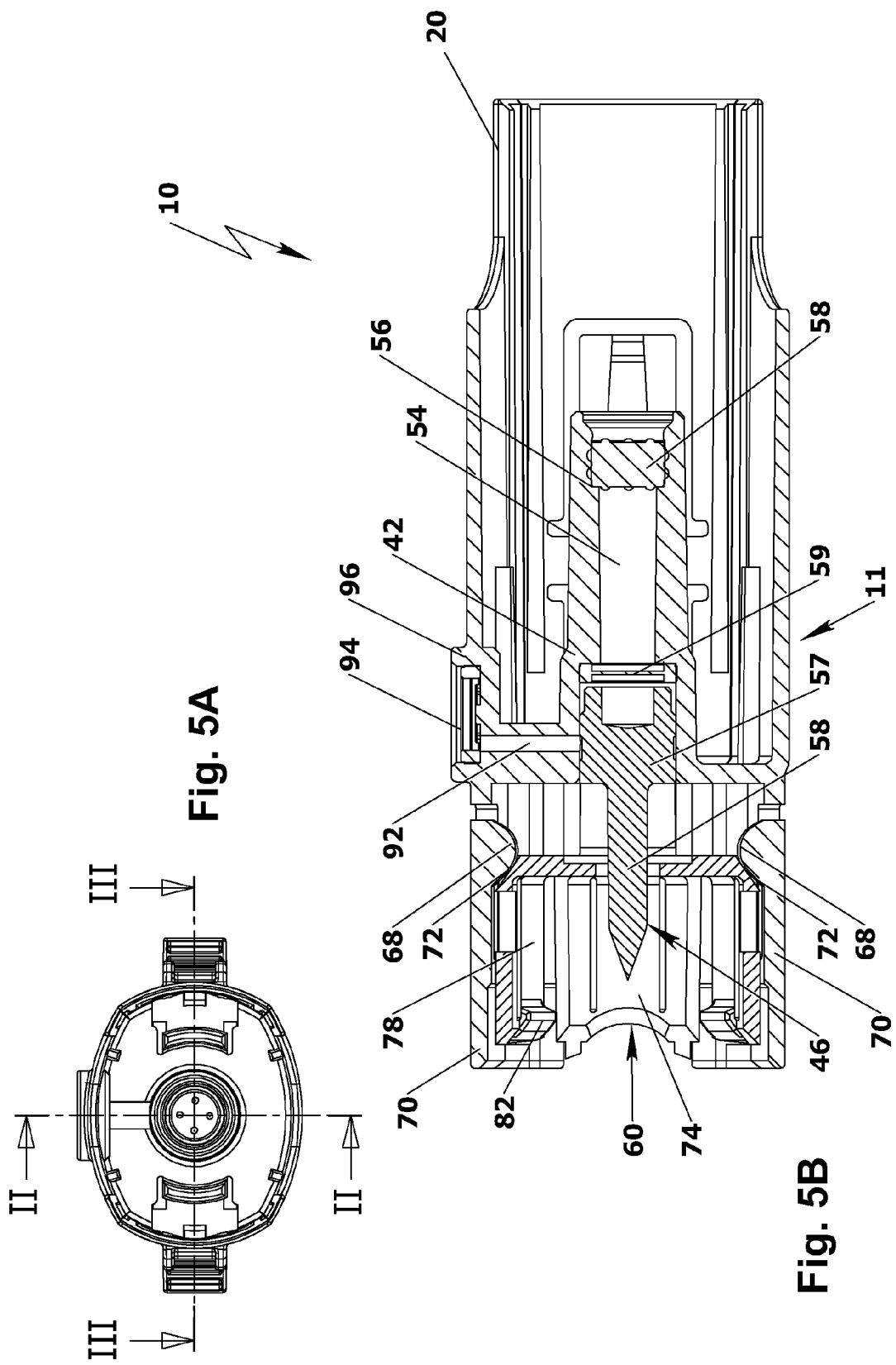
FIG. 5A is an end view of FIG. 3.
FIG. 5B is a sectional illustration along section line II-II of FIG. 5A.
Figure 6:
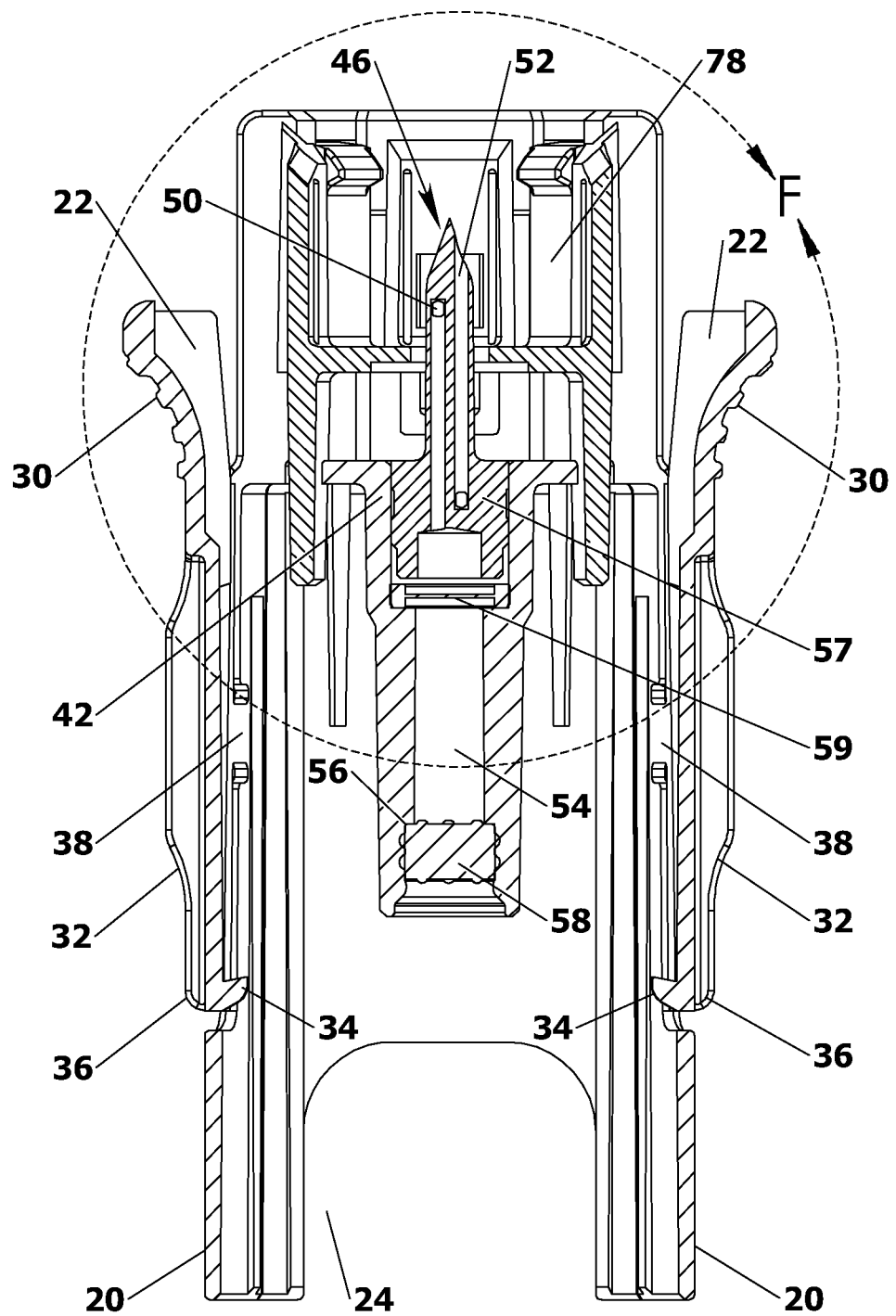
FIG. 6 is a sectional illustration along section line III-III of FIG. 5A.
Figure 7:
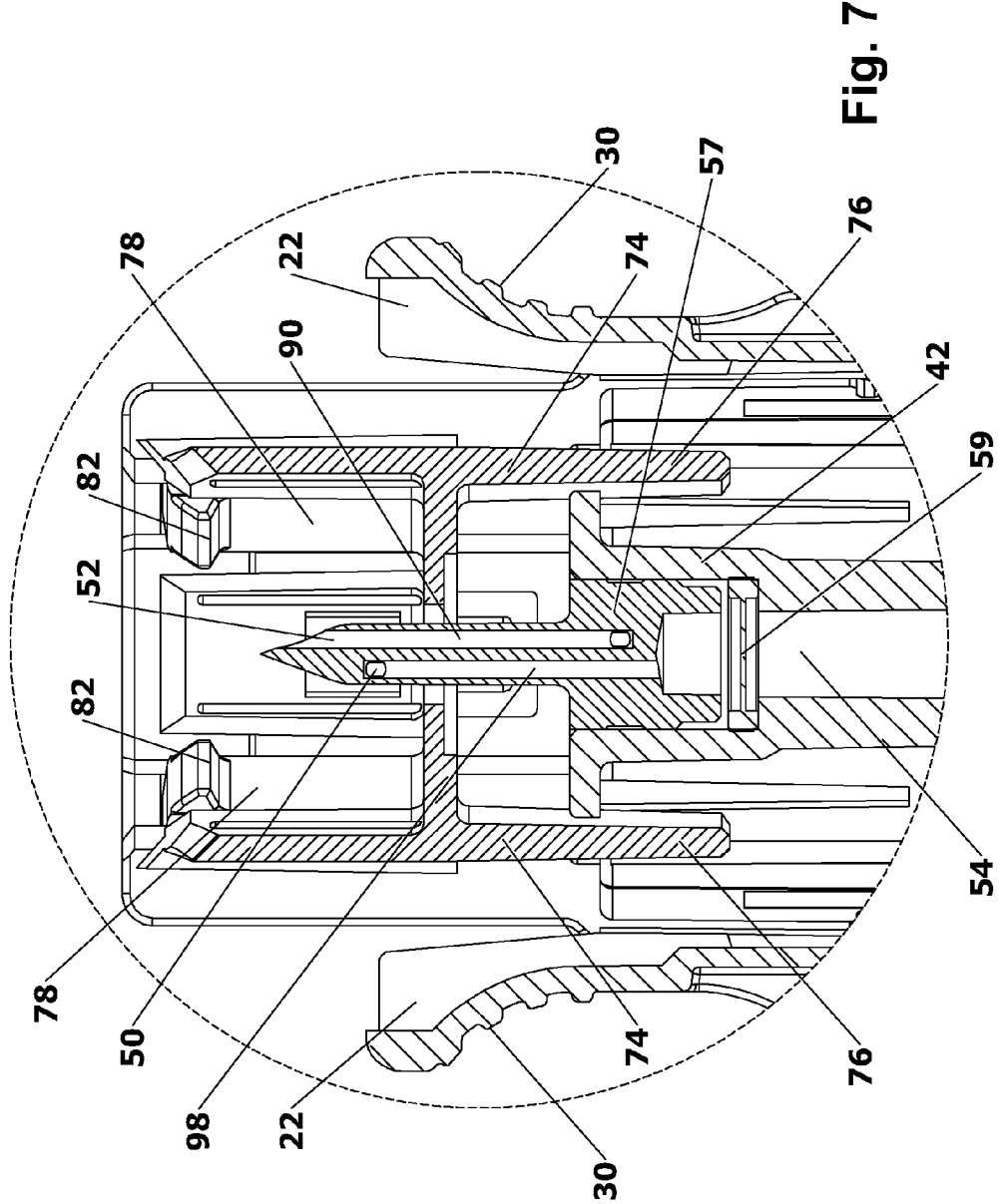
FIG. 7 is an enlarged view of area "F" of FIG. 6.
Figure 8A:
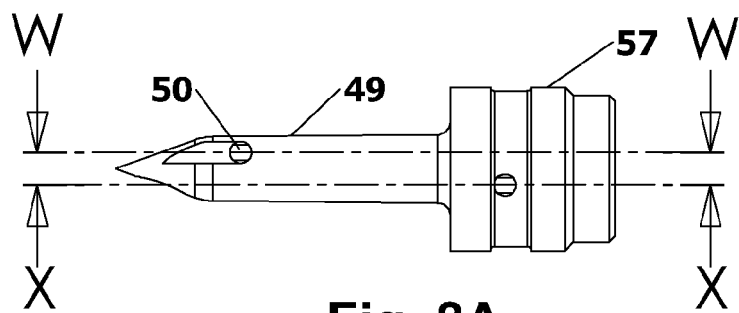
FIGS. 8A and 8B are side views, from opposite sides, of a spike for piercing a stopper of a conventional vial.
Figure 8B:
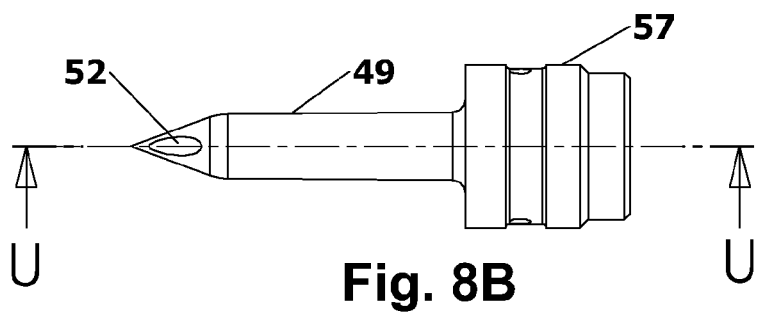
Figure 9A:
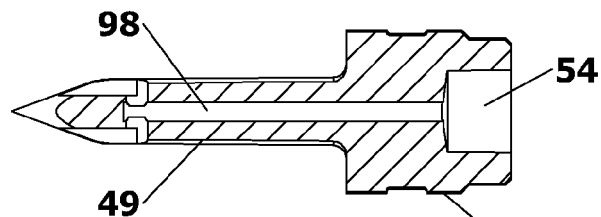
FIGS. 9A-9C are sectional views of FIG. 8A along section line "W"; of FIG. 8A along section line "X" and FIG. 8B along section line "U", respectively.
Figure 9B:
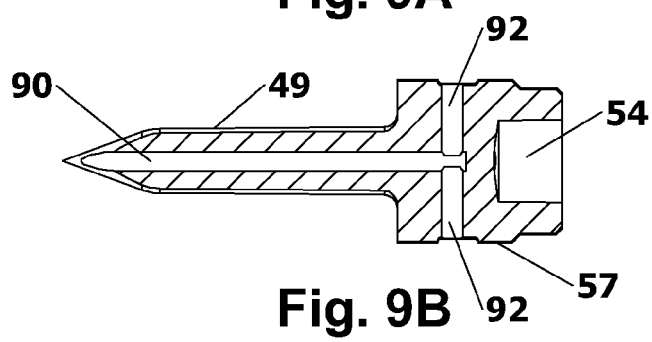
Figure 9C:
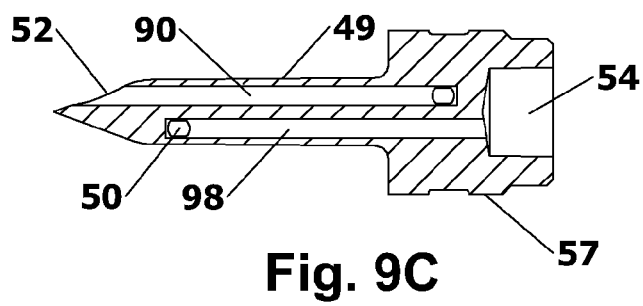

Dual-sleeved member 11 has a generally circular cylindrical forward facing sleeve 12, which is configured to enclose crown 60. Sleeve 12 is formed with a pair of opposing leafs 14 (FIG. 4). Integrally formed with sleeve 12, and facing in the opposite direction, is a generally rectangular cylindrical rearward facing sleeve 16 having curved side walls 18 and curved edge walls 20. A pair of hinged finger engagement portions 22 is integrally formed within edge walls 20. Side walls 18 are formed with rearward facing cutouts 24.

Hinged finger engagement portions 22 each include a generally planar portion 26 having an outwardly curved forward end 28, with a finger engagement surface 30, and raised side edges 32 extending along both sides of portion 26. An inwardly facing retaining protrusion 34 (FIG. 6) is located on an inwardly facing surface of a rearward end 36 of each finger engagement portion 22. Each of inwardly facing retaining protrusions 34 generally correspond a left and a right side vial adaptor engaging recess 1041 when vial adaptor 10 is positioned completely and properly on the forward end of forward housing 1040. A pair of integrally formed side hinges 38 supports planar portion 26 in an elongate cut out 40 formed in each of edge walls 20.

Generally where forward facing sleeve 12 and rearward facing sleeve 16 meet, there is an internal bulkhead 42 having defined at its center a dual-conduit spike 46, which extends forwardly. In use, a needle 49 of spike 46 punctures the elastomeric seal of vial 1010 (FIG. 1), to enable fluid communication between the interior of the vial and the interior of syringe 1046 (FIG. 1) via a medicine conduit inlet 50 adjacent though slightly inboard of a forward end of spike 46. There is also communication between the interior of the vial and the ambient air, via an air conduit outlet 52 formed adjacent the tip of spike 46. This communication takes place only after the vial adaptor 10 moves rearwardly along axis A1 (FIG. 3) and hypodermic needle 1048 of syringe 1046 pierces the septum 58 such that the needle tip is inside lumen 54.

Extending rearwardly from bulkhead 42 into the interior of rearward facing sleeve 16 is a generally cylindrical fluid passageway defining lumen 54 which has at a rearward end thereof a septum receiving recess 56 in which a septum 58 is located. At the other end of bulkhead 42, a base 57 of spike 46 is held, typically in association with a seal 59.

Crown 60 is adapted to correspond to and slidingly and reversibly engage with the interior of opposing leafs 14 of forward facing sleeve 12. Crown 60 is in the form of a generally cylindrical sleeve-like portion whose interior configuration is adapted to correspond to crimped member 1014 of the vial 1010, for releasably holding the vial. Crown 60 has an annular base 62 at an end thereof whereby the overall configuration of the crown is generally cup-shaped. In the center of base 62 is an aperture through which spike 46 passes.

The cylindrical sleeve-like portion of crown 60 is defined by three sets of parallel curved strips slightly spaced apart from each other and connected to base 62. A first set of strips is a pair of opposing strips 64 each of which is hingedly connected to base 62 and has a recess or aperture 66. Apertures 66 are adapted to releasably receive a pair of projections 68 each projecting from opposing hinged strips 70 formed in the leaves 14 of forward facing sleeve 12 of the engagement member 11. Where strips 64 connect to base 62 is a chamfer 72 to ease sliding of projections 68 upon strips 64 prior to the projections entering into apertures 66.

A second portion of the cylindrical sleeve-like portion of crown 60 is defined by a second pair of opposing strips 74 rigidly connected at base 62 at an intermediate point along the strips whereby each strip has an extension 76 extending below the base portion. The extensions 76 are designed so they push needle guard 1030 (FIG. 1) rearward when vial 10 is inserted into (crown 60 of) vial adaptor 10, which in turn disengages plunger locking element 1090 (FIG. 1) from plunger 1049 (FIG. 1) to enable forward movement of the plunger.

A third portion of the cylindrical sleeve-like portion of crown 60 is defined by a set of four strips 78, each of which is hingedly connected to base 62 and each of which has a dually projecting bulb 80 with an outwardly projecting portion 83 engagable with four corresponding apertures 81, which are disposed adjacent the free ends of leaves 14; two apertures in each leaf. Each bulb 80 also has an inwardly projecting portion 82 adapted to slide over and hold crimped member 1014 of vial 1010.

Preferably, some or all of the strips 64, 74 and 78 have one or more ribs, for example, ribs 84 of opposing strips 74, for reinforcing those strips, if required, and easing and ensuring proper alignment of crown 60 within forward end 12; e.g., wherein ribs 84 slidingly interface with wings 86.

Needle 49 of spike 46 includes a longitudinal air conduit 90 (FIG. 7) extending from air conduit outlet 52 to an air conduit extension 92 (FIG. 5B) whereby there is a passageway between air conduit outlet 52 and a filter 94 seated in a filter housing 96. Parallel to air conduit 90 is a medication conduit 98 extending from medicine conduit inlet 50 to lumen 54.

Figure 10:
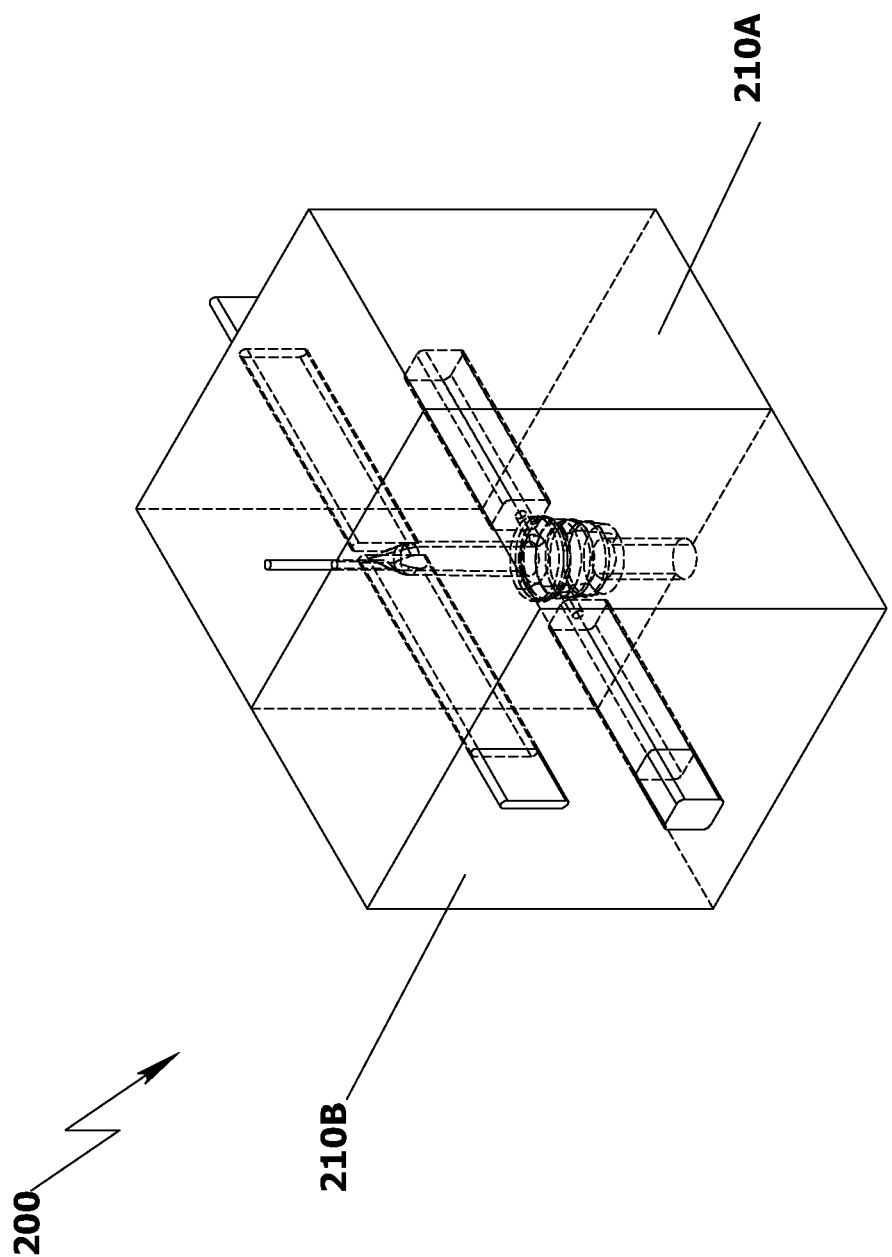

Spike Manufacturing Method:

FIGS. 10 and 11 respectively showing isometric and exploded views of an assembly 200 of the molding parts used in a preferred embodiment of a method of manufacturing spike 46. The hidden edges in FIG. 10 are shown by dashed lines. Assembly 200 includes molds 210A and 210B, having structured recesses for embodying the exterior shape 212 (shown in dashed line font in FIG. 11) of spike 46.

Assembly 200 includes a longitudinal pin 214 for the formation of longitudinal air conduit 90, and a longitudinal pin 216 for the formation of longitudinal medication conduit 98. Lateral pins 218A and 218B are used to form medication conduit inlet 50, and lateral pins 220A and 220B are used to form the lateral air conduit extensions 92.

The molding process is preferably performed as follows; initially, molds 210A and 210B are engaged to each other. Longitudinal pins 214 and 216 are then introduced into (between) molds 210A and 210B. Subsequently lateral pins and 218A, 218B, 220A and 220B are introduced until semi-circumferential recesses 222 (FIG. 11) of those pins interface with longitudinal pins 214 and 216. A molten polymer (not shown) is thence injected into mold assembly 200, and then cooled, to form bi-functional spike 46.

It should be noted that pins 214 and 216 are not longitudinally constrained by molds 210A and 210B and lateral pins 218A, 218B, 220A and 220B whereby the possibility of deformation or buckling of conduits 90 and 98 as a result of thermal influences is reduced or prevented.

Pins 214 and 216 are typically only about 0.7 millimeters in diameter and hence may easily deform during the molding process, particularly during multiple repetitions of the process. In order to prevent such deformation and form air aperture 52 and lateral air conduit extensions 92, lateral pins 220A and 220B are used for centering and stabilizing longitudinal pin 214 and lateral pins 218A and 218B are used for centering and stabilizing longitudinal pin 216, as well as forming the medication conduit inlet 50.

To elaborate on the centering and stabilizing feature of lateral pins 218A, 218B, 220A and 220B, reference is now made to FIG. 12. As seen in enlarged views A and B, lateral pins 218A and 220A have semi-circumferential recesses 222 at their tips, conforming respectively to the exterior surfaces of longitudinal pins 214 and 216. Lateral pins 218B and 220B also have respectively matching semi-circumferential recesses at their tips (not visible). These semi-circumferential recesses 222 at the tips of the lateral pins 218A, 218B, 220A and 220B help prevent a substantial lateral displacement of the pins 214 and 216, while allowing for axial expansion thereof, which may result from the increase in temperature during the molding process.

Use/Operation:

During use of vial adaptor 10, crown 60 translates between two positions: a position wherein outwardly projecting potions 83 of bulbs 80 project into respective corresponding apertures 81 of leaves 14 of forward facing sleeve 12, which occurs when vial 1010 is removed from crown 60 of vial adaptor 10; and a position wherein projections 68 projecting from opposing hinged strips 70 slide over chamfers 72 and project into respective corresponding apertures 66 of opposing strips 64, which occurs upon pushing the vial axially into the adaptor.

To withdraw medicine from vial 1010 using adaptor 10, rearward facing sleeve 16 is first placed over the front portion of forward housing 1040 whereby inwardly facing retaining protrusions 34 of hinged finger engagement portions 22 enter recesses 1041 forcing hypodermic needle 1048 of syringe 1046 to pierce the septum 58 such that the needle tip is inside lumen 54. At this point, crown 60 is typically in a position wherein outwardly projecting portions 83 of bulbs80 project into respective corresponding apertures 81 of leaves 14 of forward facing sleeve 12, which occurs when vial 1010 is removed from crown 60 of vial adaptor 10.

Then vial 1010 is pushed into crown 60 of adaptor 10 causing spike 46 to pierce the vial's stopper. When vial 1010 is pushed into crown 60, crimped member 1014 slides over inwardly projecting portion 82, urging strips 78 to bend outward about their hinged connection with base 62. Vial 1010 is properly seated in crown 60 when projections 68 projecting from opposing hinged strips 70 have slid over chamfers 72 and project into respective corresponding apertures 66 of opposing strips 64. Vial 1010 is held in place by inwardly projecting portion 82 as strips 78 are not free to bend outward because outwardly projecting portions 83 interfacing with the inside of sleeves 14 do not allow this.

Plunger 1049 is then withdrawn backward to withdraw medication from vial 1010, while filtered ambient air enters the vial. In this position, extensions 76 of opposing strips 74 press needle guard 1030 backward such that upwardly facing protrusions align with bottom surface 1826 resulting in plunger locking element 1090 pivoting about its axis 1810 whereby plunger engaging protrusion 1802 disengages from teeth 1478 and plunger 1049 can also be moved forward. If a first vial 1010 with a liquid (solvent or carrier) were to be replaced with a second vial, for example, a vial with a powdered medication, the liquid could be injected into the second vial, where it would dissolve the powder, and then the resulting solution could be withdrawn into syringe 1046 of injector 1008 for injection.

When vial 1010 is removed from crown 60 of vial adaptor 10, the crown is returned to its initial location in that the crown is moved by inwardly projecting portions 82 in the neck of the vial until outwardly projecting portion 83 to apertures 81 at which point inwardly projecting portions 82 are released from the vial's neck. Crown 60 is stopped and allows the vial 1010 to slide out. In the process, projections 68 exit opening apertures 66 and returns to its initial location opposite chamfers 72. Movement of the crown 60 to its initial location causes plunger 1049 to re-lock.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. A combination of an injector and a vial adaptor for releasably holding a vial comprising:
   an injector plunger arranged along a longitudinal axis;
   a vial adaptor sleeve member arranged along said longitudinal axis; and
   a vial engaging element operative to slidingly translate within said vial adaptor sleeve member in an axial direction along said longitudinal axis, releasably hold said vial and allow axial movement along said longitudinal axis of said plunger relative to said vial adaptor sleeve member,
   said vial engaging element being operative, in a non-vial engagement orientation, to retain said injector plunger in a locked position relative to said vial adaptor sleeve member against axial movement along said longitudinal axis in at least one axial direction of said injector plunger, and in a vial engagement orientation, to allow said axial movement along said longitudinal axis of said plunger relative to said vial adaptor sleeve member in at least one axial direction of said injector plunger.

2. A combination of an injector and a vial adaptor according to claim 1, wherein said vial adaptor sleeve member includes a vial stopper piercing member comprising:
   a first conduit; and
   a second conduit to neutralize pressure in the vial.

3. A combination of an injector and a vial adaptor according to claim 2 wherein said second conduit extends from a point adjacent a piercing end of said vial stopper piercing member to a point adjacent to an opposite end of said vial stopper piercing member, and said first conduit extends from a point set back from said piercing end of said vial stopper piercing member to a point adjacent to said opposite end thereof.

4. A combination of an injector and a vial adaptor according to claim 2, wherein said second conduit is arranged for ambient air inlet and said first conduit is arranged for medicine transfer.

5. A combination of an injector and a vial adaptor according to claim 3, wherein said second conduit is configured to allow ambient air to enter said vial.

6. A combination of an injector and a vial adaptor according to claim 3, further comprising a base at said opposite end that connects said vial stopper piercing member to said vial adaptor sleeve member.

7. A combination of an injector and a vial adaptor according to claim 1 and also comprising a vial stopper piercing member having a piercing end and an opposite end, said vial stopper piercing member being arranged along said longitudinal axis.

8. A combination of an injector and a vial adaptor according to claim 7 wherein said vial stopper piercing member includes:
   a first conduit; and
   a second conduit to neutralize pressure in the vial,
   said first conduit and said second conduit being spaced apart and arranged in parallel to said longitudinal axis.

9. A combination of an injector and a vial adaptor according to claim 7 wherein the vial engaging element has a central aperture through which said vial stopper piercing member extends.

10. A combination of an injector and a vial adaptor according to claim 1 wherein the vial engaging element has at least one outwardly projecting protrusion corresponding with at least one aperture extending through said sleeve member.

11. A combination of an injector and a vial adaptor according to claim 1 wherein said vial engaging element has at least one inwardly projecting protrusion adapted to slide over and hold said vial relative to said vial engaging element.

12. A combination of an injector and a vial adaptor for releasably holding a vial comprising:
   an injector plunger;
   a vial adaptor sleeve member including:
      a vial stopper piercing member comprising:
         a first conduit; and
         a second conduit to neutralize pressure in the vial, said second conduit extending from a point adjacent a piercing end of said vial stopper piercing member to a point adjacent to an opposite end of said vial stopper piercing member, and said first conduit extending from a point set back from said piercing end of said vial stopper piercing member to a point adjacent to said opposite end thereof, and
      a base at said opposite end that connects said vial stopper piercing member to said vial adaptor sleeve member;
   a vial engaging element operative to slidingly translate within said vial adaptor sleeve member, releasably hold said vial and allow axial movement of said plunger relative to said vial adaptor sleeve member, said vial engaging element being operative, in a non-vial engagement orientation, to retain said injector plunger in a locked position relative to said vial adaptor sleeve member against axial movement in at least one axial direction of said injector plunger, and in a vial engagement orientation, to allow said axial movement of said plunger relative to said vial adaptor sleeve member in at least one axial direction of said injector plunger, and
   a plunger locking element,
   the vial engaging element having at least one strip extending through an aperture formed in said base to disengage said plunger locking element from said injector plunger.

13. A combination of an injector and a vial adaptor for releasably holding a vial comprising:
   an injector plunger;
   a vial adaptor sleeve member; and
   a vial engaging element operative to slidingly translate within said vial adaptor sleeve member, releasably hold said vial and allow axial movement of said plunger relative to said vial adaptor sleeve member,
   said vial engaging element being operative, in a non-vial engagement orientation, to retain said injector plunger in a locked position relative to said vial adaptor sleeve member against axial movement in at least one axial direction of said injector plunger, and in a vial engagement orientation, to allow said axial movement of said plunger relative to said vial adaptor sleeve member in at least one axial direction of said injector plunger,
   the vial engaging element having at least one outwardly projecting protrusion corresponding with at least one aperture extending through said sleeve member,
   said vial engaging element being selectably positionable in a first position in which said at least one protrusion is inserted into said at least one aperture and in a second position in which said at least one protrusion is disengaged from said at least one aperture; and forward axial movement of said plunger relative to said vial adaptor sleeve member is allowed in said second position.

14. A combination of an injector and a vial adaptor for releasably holding a vial comprising:

an injector plunger;

a vial adaptor sleeve member; and a vial engaging element operative to slidingly translate within said vial adaptor sleeve member, releasably hold said vial and allow axial movement of said plunger relative to said vial adaptor sleeve member, said vial engaging element being operative, in a non-vial engagement orientation, to retain said injector plunger in a locked position relative to said vial adaptor sleeve member against axial movement in at least one axial direction of said injector plunger, and in a vial engagement orientation, to allow said axial movement of said plunger relative to said vial adaptor sleeve member in at least one axial direction of said injector plunger, said vial engaging element having at least one inwardly projecting protrusion adapted to slide over and hold said vial relative to said vial engaging element, the vial engaging element having at least one outwardly projecting protrusion corresponding with at least one aperture extending through said sleeve member; and said at least one inwardly projecting protrusion being adapted to slide over and hold said vial relative to said vial engaging element and lock said vial in said vial engaging element when said at least one outwardly projecting protrusion is disengaged from said at least one aperture.

* * * * *